(12) United States Patent
Zhou et al.

(10) Patent No.: US 10,328,290 B2
(45) Date of Patent: Jun. 25, 2019

(54) WEEPING BALLOON CATHETER WITH ULTRASOUND ELEMENT

(71) Applicant: Muffin Incorporated, West Lafayette, IN (US)

(72) Inventors: Yun Zhou, West Lafayette, IN (US); Peter S. McKinnis, West Lafayette, IN (US); Sarah Robbins, Lafayette, IN (US); Neal E. Fearnot, West Lafayette, IN (US)

(73) Assignee: Muffin Incorporated, West Lafayette, IN (US)

(*) Notice: Subject to any disclaimer, the term of this patent is extended or adjusted under 35 U.S.C. 154(b) by 542 days.

(21) Appl. No.: 13/956,407

(22) Filed: Aug. 1, 2013

(65) Prior Publication Data

US 2014/0039358 A1 Feb. 6, 2014

Related U.S. Application Data

(60) Provisional application No. 61/679,235, filed on Aug. 3, 2012.

(51) Int. Cl.
*A61B 17/22* (2006.01)
*A61N 7/00* (2006.01)
(Continued)

(52) U.S. Cl.
CPC .......... *A61N 7/022* (2013.01); *A61B 17/2202* (2013.01); *A61M 25/1011* (2013.01);
(Continued)

(58) Field of Classification Search
CPC combination set(s) only.
See application file for complete search history.

(56) References Cited

U.S. PATENT DOCUMENTS

| 5,800,392 A * | 9/1998 | Racchini | A61M 25/10 604/103.01 |
| 6,210,356 B1 * | 4/2001 | Anderson | A61K 41/0047 601/2 |

(Continued)

FOREIGN PATENT DOCUMENTS

| WO | WO 95/05866 | 3/1995 |
| WO | WO 98/40033 | 9/1998 |

(Continued)

OTHER PUBLICATIONS

International Search Report dated Nov. 14, 2013 as issued in related application, PCT/US2013/053189, 24 pages.
(Continued)

*Primary Examiner* — Christopher L Cook
(74) *Attorney, Agent, or Firm* — Woodard, Emhardt, Henry, Reeves & Wagner, LLP

(57) ABSTRACT

Systems and methods for treating a blood clot positioned within a blood vessel are disclosed. In one embodiment, a balloon member is positioned on a distal end region of a catheter and an ultrasound emitting element is positioned within the balloon member and arranged for actively emitting ultrasound. In some exemplary embodiments, the disclosure provides a multi-wall balloon member and a multi-lumen catheter with at least one and/or all cavities of the balloon member arranged for heat transfer with the ultrasound emitting element. The disclosure also provides catheter arrangements with an ultrasound emitting element arranged to heat tissue adjacent to the balloon member. Additionally, in some embodiments, at least one and/or all walls of the balloon member have apertures arranged to release a therapeutic agent such as a thrombolytic drug.

35 Claims, 10 Drawing Sheets

(51) Int. Cl.
*A61N 7/02* (2006.01)
*A61M 25/10* (2013.01)
*A61M 37/00* (2006.01)
*A61B 18/00* (2006.01)

(52) U.S. Cl.
CPC ............... *A61M 37/0092* (2013.01); *A61B 2017/22001* (2013.01); *A61B 2017/22021* (2013.01); *A61B 2017/22054* (2013.01); *A61B 2017/22062* (2013.01); *A61B 2017/22084* (2013.01); *A61B 2017/22088* (2013.01); *A61B 2018/00023* (2013.01); *A61M 25/1006* (2013.01); *A61M 2025/105* (2013.01); *A61M 2025/1013* (2013.01); *A61M 2025/1086* (2013.01)

(56) References Cited

U.S. PATENT DOCUMENTS

| | | |
|---|---|---|
| 6,440,158 B1 | 8/2002 | Saab |
| 6,524,274 B1* | 2/2003 | Rosenthal ............... A61F 2/90 604/96.01 |
| 6,974,474 B2 | 12/2005 | Pavcnik et al. |
| 7,201,737 B2 | 4/2007 | Hansmann et al. |
| 8,182,446 B2 | 5/2012 | Schaeffer et al. |
| 2004/0082859 A1* | 4/2004 | Schaer ............... A61B 8/4281 600/459 |
| 2007/0005049 A1* | 1/2007 | Comben ............... A61B 18/082 606/31 |
| 2009/0036831 A1 | 2/2009 | Howat |
| 2010/0069900 A1 | 3/2010 | Shirley et al. |
| 2010/0113949 A1* | 5/2010 | Sathyanarayana ... A61B 5/0215 600/500 |
| 2010/0292641 A1 | 11/2010 | Wijay et al. |
| 2010/0031817 A1 | 12/2010 | Schaeffer et al. |
| 2011/0060275 A1 | 3/2011 | Christiansen |
| 2011/0060276 A1 | 3/2011 | Schaeffer et al. |
| 2011/0130719 A1 | 6/2011 | Aggerholm |
| 2011/0313400 A1 | 12/2011 | Boatman |
| 2012/0143054 A1 | 6/2012 | Eaton et al. |
| 2013/0184791 A1* | 7/2013 | Wallsten ............... A61F 7/123 607/105 |

FOREIGN PATENT DOCUMENTS

| | | | |
|---|---|---|---|
| WO | WO 2010/120620 | * | 10/2010 |
| WO | WO 2011/094379 A1 | | 8/2011 |
| WO | WO 2012/003369 A2 | | 1/2012 |

OTHER PUBLICATIONS

Shaw et al., "Arrhenius temperature dependence of in vitro tissue plasminogen activator thrombolysis", Phys Med Biol. Jun. 7, 2007; 52(11) 2953-2967.

* cited by examiner

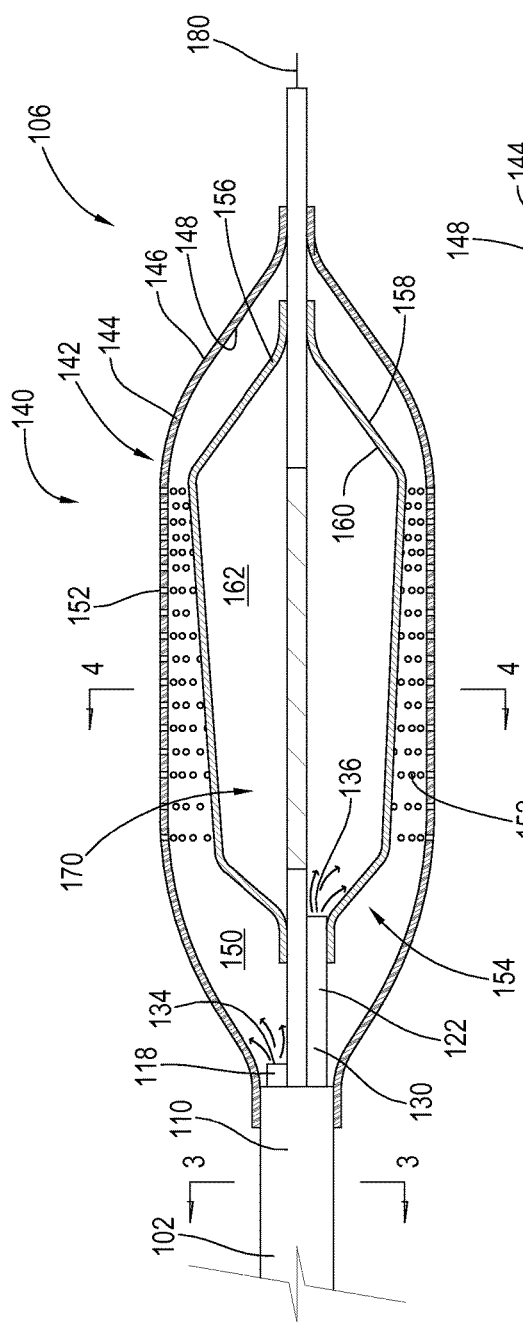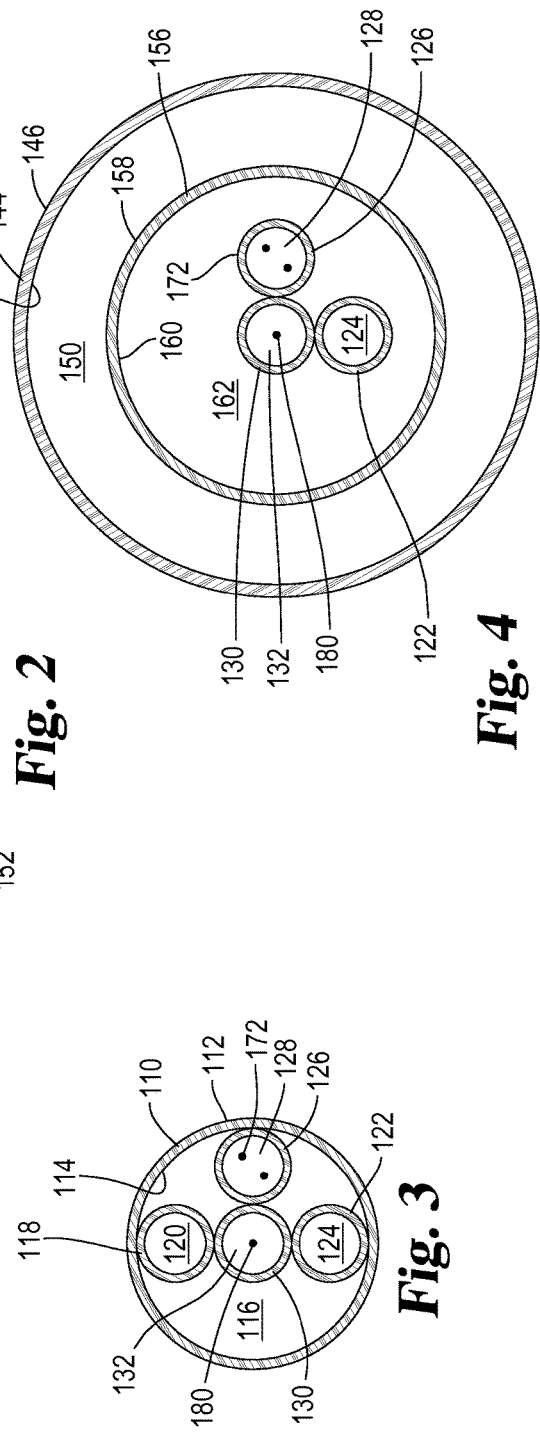

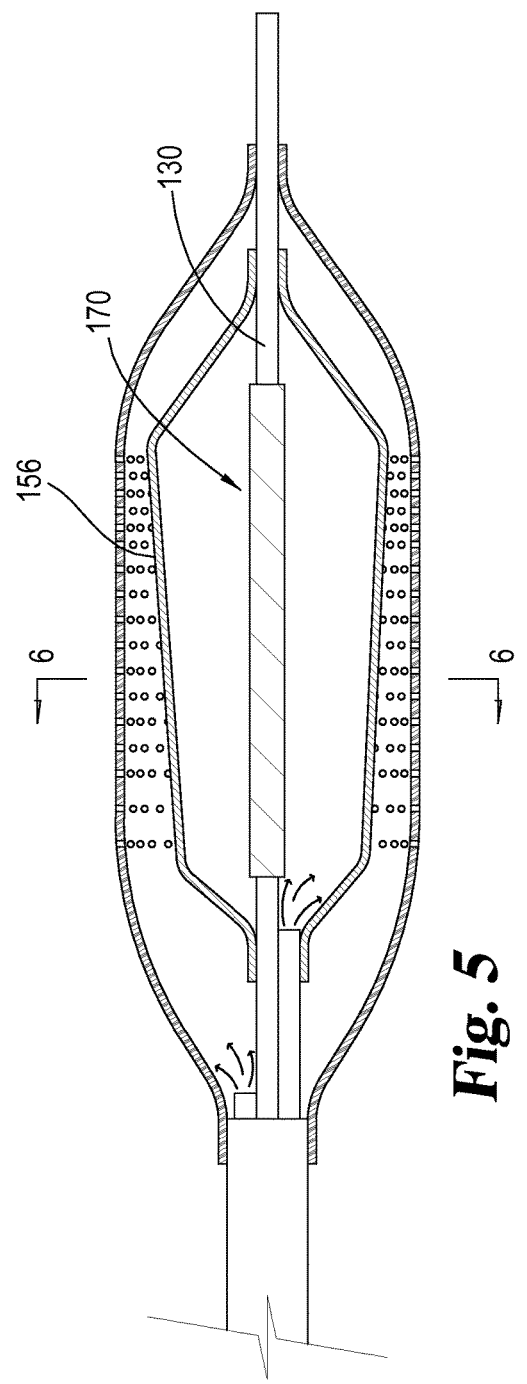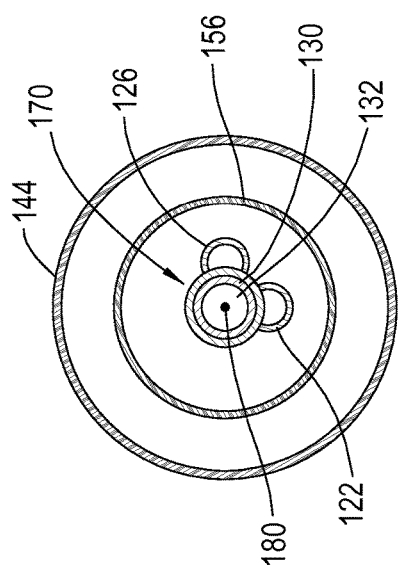

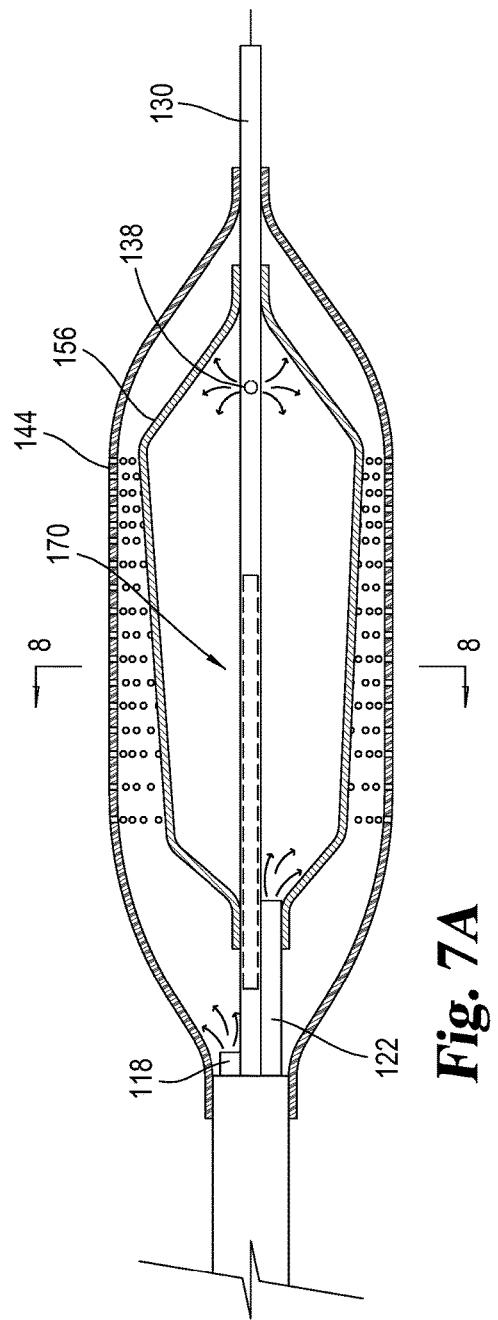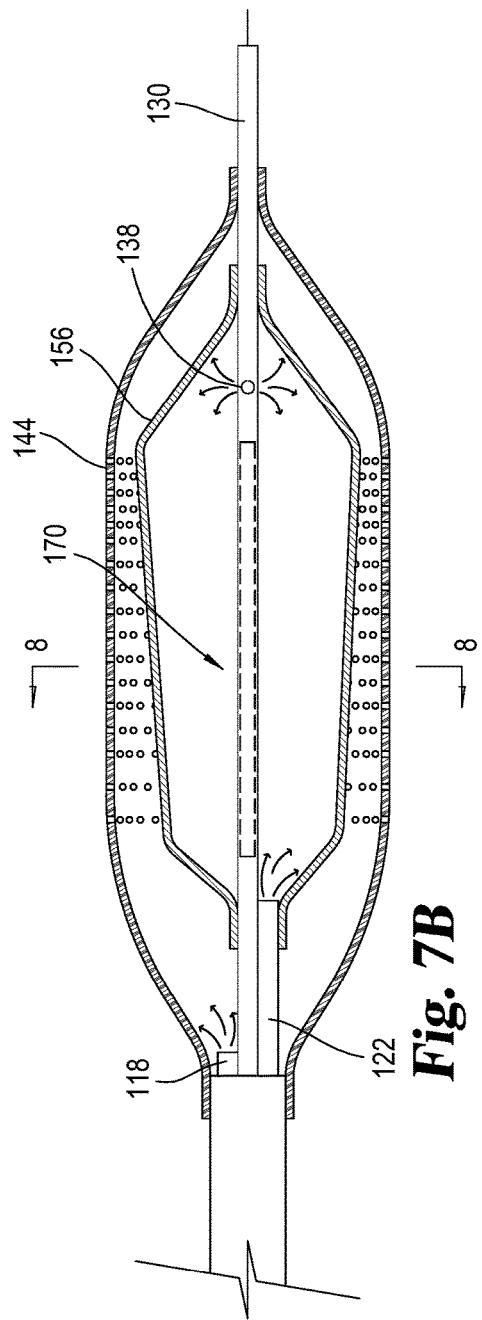

WEEPING BALLOON CATHETER WITH ULTRASOUND ELEMENT

CROSS-REFERENCE TO RELATED APPLICATIONS

This application claims the benefit of U.S. Provisional Application No. 61/679,235, filed Aug. 3, 2012, which is hereby incorporated by reference in its entirety.

FIELD OF THE INVENTION

The present disclosure pertains generally to devices and methods for treating a blood clot in a blood vessel of a patient.

BACKGROUND

Thrombosis is the formation of blood clot(s) within the vasculature that obstructs the flow of blood. The level of obstruction can range from minimal to fully occluded. These blood clots, or thrombi, can be fixed to a vessel wall. These clots are known to be created and vary in size in different parts of the anatomy. Veins in the legs, such as the femoral vein or the popliteal vein, are typically high incident areas for developing thrombosis in patient groups with certain risk factors.

Thrombus formation in the deep veins of the legs, such as the femoral and popliteal veins, is known as deep vein thrombosis (DVT). High risk patient groups for developing DVT include trauma patients, orthopedic surgery patients, neurosurgery patients, or patients having medical conditions requiring bed rest or immobilization. Sitting in the same position for long periods of time, which can occur during lengthy air travel or long car trips, can increase risk factors that lead to the development of DVT.

During and after such medical conditions or situations that present a heightened risk of DVT, there is an increased chance that a more serious condition known as a Pulmonary Embolism (PE) can occur. When large thrombi are formed within the patient's vasculature, they may disrupt or occlude local blood flow or even break free, i.e., embolize, and travel through the vasculature toward the patient's heart and lungs. This can block blood flow into the lungs, known as a pulmonary embolism, which can ultimately lead to death. In other circumstances, the dislodged portion may be caught within a different portion of the vasculature to substantially or totally occlude blood flow through that portion. Obstruction of blood flow within the vascular is an undesirable situation.

Due to the problematic disruption of localized blood flow (or potential total occlusion of flow) through a portion of the patient's vasculature, and the additional dangerous potential of dislodged portions of a thrombus flowing into the patient's heart then through the pulmonary artery to the lungs, it is often medically necessary to eliminate or reduce the size of a thrombosis when noted within the vasculature.

SUMMARY

The present disclosure relates to medical devices and more particularly to medical devices adapted to remove or reduce a deep vein thrombosis (DVT), restenosis, or other occlusions disposed within a patient's vasculature or within other systems such as the gastrointestinal tract, genitourinary system and sinus cavities. In some aspects, the present disclosure provides devices and methods for releasing a therapeutic agent into a blood clot and delivering therapeutic ultrasound. In some embodiments, a medical device for treating a blood clot in a blood vessel, comprises: a multi-lumen catheter having a multi-wall balloon positioned thereon and an ultrasound emitting element positioned within the multi-wall balloon; wherein the ultrasound emitting element is arranged for actively emitting ultrasound. In various embodiments, the ultrasound emitting element can be positioned on an outer surface, in a wall, and/or within a lumen of the catheter. Additionally, in some instances, the ultrasound emitting element is movable within the catheter, and, in some embodiments, the ultrasound emitting element is arranged to heat a fluid positioned within the multi-wall balloon.

The present disclosure also provides a medical device for treating a blood clot in a blood vessel, comprising: a multi-lumen catheter having a balloon with a porous balloon wall positioned thereon and surrounding an ultrasound emitting element; wherein the ultrasound emitting element is arranged for actively emitting ultrasound. In some instances the porous balloon wall comprises apertures arranged to release a therapeutic agent. Additionally, in some embodiments, the apertures communicate with a balloon cavity.

In some aspects, the present disclosure teaches a medical device for treating a blood clot in a blood vessel, comprising: a catheter having first and second lumens, a balloon member positioned on a distal portion of the catheter and having inner and outer balloons defining inner and outer balloon cavities, and an ultrasound emitting element positioned within the inner balloon cavity; the first and second lumens extending from a proximal end region of the catheter to a distal end region of the catheter and communicating with the inner and outer balloon cavities; and wherein the ultrasound emitting element actively emits ultrasound through the inner balloon cavity, into the outer balloon cavity, and out of the outer balloon cavity into the thrombus adjacent to the outer balloon. In some instances, the inner balloon is arranged to transmit heat from a fluid within the inner balloon cavity to a fluid within the outer balloon cavity. Additionally, some embodiments have a first temperature-control lumen within the catheter and are arranged to transmit a temperature-control fluid between a proximal end region and a distal end region of the catheter. Optionally, a second temperature-control lumen within the catheter, in communication with the first temperature-control lumen, and arranged to transmit a temperature-control fluid between the proximal end region and the distal end region of the catheter; wherein the first and second temperature-control lumens can cooperate to circulate a fluid between the proximal and distal end regions of the catheter.

The present disclosure provides a method of treating a blood clot in a blood vessel, comprising: positioning adjacent to the blood clot a distal portion of a catheter having a balloon member having inner and outer balloons and an ultrasound emitting element positioned within the inner balloon; inflating the inner balloon of the balloon member; inflating the outer balloon of the balloon member; releasing a therapeutic agent into the blood clot from a wall of the outer balloon; and emitting ultrasound from the ultrasound emitting element positioned so as to increase penetration and diffusion of the therapeutic agent into the blood clot to treat the blood clot. In some instances, the releasing of a therapeutic agent is synchronized with the emitting ultrasound from the ultrasound emitting element.

Further forms, objects, features, aspects, benefits, advantages, and embodiments of the present invention will become apparent from a detailed description and drawings provided herewith.

BRIEF DESCRIPTION OF THE DRAWINGS

FIG. 2 is a cross-sectional view through the walls of a balloon member positioned on the distal portion of the catheter of FIG. 1.

FIG. 3 is a cross-sectional view of the catheter along line 3-3 of FIG. 2.

FIG. 4 is a cross-sectional view of the balloon member along line 4-4 of FIG. 2.

FIG. 5 is a cross-sectional view through the walls of a balloon member of one embodiment.

FIG. 6 is a cross-sectional view along line 6-6 of the balloon member in FIG. 5.

FIGS. 7a and 7b are cross-sectional views through the walls of a balloon member of one embodiment, showing movement of the ultrasound emitting element within the catheter.

DESCRIPTION OF THE ILLUSTRATED EMBODIMENTS

Figure 1:
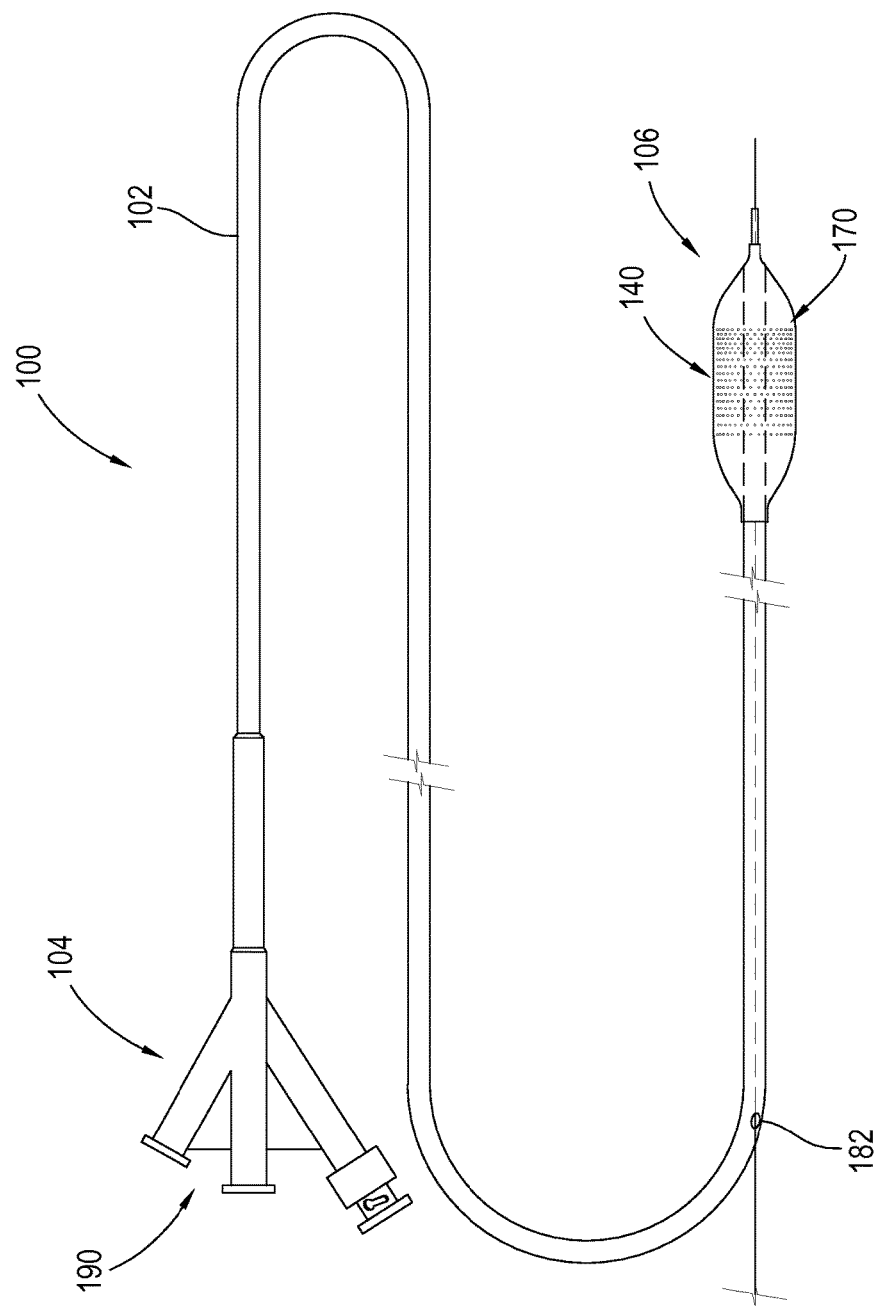
FIG. 1 is a plan view of one embodiment of a treatment system having a catheter, a balloon member, and a connector.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

With respect to the specification and claims, it should be noted that the singular forms "a", "an", "the", and the like include plural referents unless expressly discussed otherwise. As an illustration, references to "a device" or "the device" include one or more of such devices and equivalents thereof. It also should be noted that directional terms, such as "up", "down", "top", "bottom", and the like, are used herein solely for the convenience of the reader in order to aid in the reader's understanding of the illustrated embodiments, and it is not the intent that the use of these directional terms in any manner limit the described, illustrated, and/or claimed features to a specific direction and/or orientation.

The disclosed embodiments and variations thereof may be used to treat a blood clot, such as by reducing or removing the blood clot, located within a blood vessel of a patient. For instance, the disclosed embodiments may be used to reduce a blood clot found within a deep vein in the leg of a patient. While some portions of the following disclosure may make reference to parts or portions of human patients, it is not intended that the present disclosure be limited to such. The disclosed embodiments and methods may be used with at least human and veterinary patients in various locations within those patients, as will be apparent to one of ordinary skill in the art.

Lytic agents are often used to treat thrombosis in the vasculature of patients. Unfortunately, in blood clots, the plasminogen receptor sites that bind with the lytic agents are buried within tightly wound fibrin strands, restricting the access of lytic agents from penetrating the clot and reaching the receptor sites. It has been discovered that applying ultrasound energy to the blood clot causes the fibrin strands to thin and allows a lytic agent to penetrate deeper into the clot and bind to receptor sites. Thus, the application of therapeutic ultrasound in combination with lytic agents increases the absorption of lytic agent by the clot, resulting in improved clot reduction. It is also known that the application of ultrasound energy increases the diffusion or mixing of the lytic agent within the treatment site.

It has also been discovered that the activity of the thrombolytic agent may be increased with an increase in temperature of the thrombolytic solution and/or the treatment site. Studies have shown that the activity of tissue plasminogen activator (tPA), a thrombolytic drug, is temperature dependent. More specifically, as demonstrated by a study of H. Schwarzenberg et al (Cardiovasc Intervent Radiol, 1998; 21:142-145), the thrombolysis efficacy of tPA monotonically increases with temperature between 30° C. and 45° C., and the time to completely lyse a clot significantly decreases with increased temperature. A theoretic model from a study of G J Shaw et al (Phys. Med. Biol. 2007; 52:2953-2967) suggests an additional 37% increase of clot mass loss for a 30 minute tPA treatment if elevating temperature from 37° C. to 43° C., or a 30% increase of clot mass loss for a 30 minute tPA treatment if elevating temperature from 35° C. to 40° C. Additionally, there is a decline in body temperature in the extremities of even healthy subjects. For example, at 37° C. rectal body temperature and 20° C. environmental temperature, body temperature of the subjects investigated was approximately 35° C. in the femoral muscles, 33° C. in the calf muscles and 27° C. in the foot (Aschoof J, Weaver R, Kern and Schale im Warmehaushalf des Menschen, (1958)45:477-481).

Aspects of the present disclosure provide devices and methods for delivering a therapeutic agent to a treatment site, such as a blood clot, in combination with the emission of therapeutic ultrasound energy. The present disclosure also provides devices and methods for delivering a therapeutic agent, such as a thrombolytic agent, prior to, during, and/or after increasing the temperature of the therapeutic agent and/or the treatment site.

FIGS. 1-4 illustrate a treatment system 100 comprising a catheter 102, a balloon member 140, an ultrasound emitting element 170 and a connector 190. The catheter 102 has a proximal end region 104 and a distal end region 106. Balloon member 140 is positioned on distal end 106 of catheter 102 and comprises an outer balloon 142 and an inner balloon 154. Outer balloon 142 has an outer balloon wall 144 having an outer surface 146 and an inner surface 148. In some instances outer balloon wall 144 has apertures 152 arranged to receive a therapeutic agent and release a therapeutic agent during and/or after expansion of outer balloon wall 144.

In some instances, at least one and/or all of apertures 152 in outer balloon wall 144 extend through the thickness of outer balloon wall 144 so as to allow fluid positioned within outer balloon cavity 150 to pass through apertures 152 and out of the balloon member 140. In other instances, at least one and/or all of apertures 152 in outer balloon wall 144 do not extend through outer balloon wall 144. For example, apertures 152 may comprise wells and/or dimples on outer surface 146 of outer balloon wall 144, opening towards the area proximal to balloon member 140 and having a closed bottom.

In some embodiments, at least one and/or all of apertures 152, such as wells and/or dimples, are arranged to retain a therapeutic agent and release the therapeutic agent prior to, during, and/or after expansion of outer balloon 142. For example, during manufacturing of treatment system 100, at least one therapeutic agent can be positioned within at least one or all of apertures 152 and retained in the opening 152 prior to desired release of the therapeutic agent during a surgical procedure. In some instances, a wall of the balloon member 140, such as outer balloon wall 144, stretches as outer balloon 142 is inflated/expanded, causing apertures 152 to open and/or increase in size to permit the release of a therapeutic agent, such as a thrombolytic drug. In some instances, at least one or all of apertures 152 are arranged for passive emission of a therapeutic agent from outer balloon cavity 150 through apertures 152 and into the area proximate to balloon member 140. In some embodiments, a therapeutic agent is coated on outer surface 146 of outer balloon wall 144, such as in a polymeric drug eluting coating, and is not limited to or not contained within apertures 152.

Inner balloon 154 comprises an inner balloon wall 156 having an outer surface 158 and an inner surface 160. Inner surface 148 of outer balloon wall 144 and outer surface 158 of inner balloon wall 156 define an annular space such as outer balloon cavity 150 arranged to receive a fluid to inflate the outer balloon 142. Similarly, inner surface 160 of inner balloon 154 and an outer surface of a portion of the catheter 102, such as fourth tubular member 130 which will be discussed later, and/or ultrasound emitting element 170 define an inner balloon cavity 162 arranged to receive a second fluid therein to inflate inner balloon 154.

In many instances, inner balloon cavity 162 and outer balloon cavity 150 are fluidly disconnected (e.g., not in fluid communication). This may be preferred in some embodiments in which it is desired that the fluids positioned within inner balloon cavity 162 and outer balloon cavity 150 not mix. For example, a contrast and/or an echogenic agent may be positioned within inner balloon cavity 162 so as to aid in the tracking and/or positioning of balloon member 140 relative to an occlusion in a blood vessel, such as a thrombosis while a therapeutic agent is positioned within the outer cavity 150 or within other systems such as the gastrointestinal tract, genitourinary system and sinus cavities. Additionally, filling outer balloon cavity 150 and not inner balloon cavity 162 with a therapeutic agent reduces the amount of therapeutic agent needed to inflate balloon member 140.

In some instances, it may be preferred that inner balloon cavity 162 and outer balloon cavity 150 are in fluid communication. For example, in some instances it may be desired that the fluid positioned within inner balloon cavity 162 be allowed to flow into outer balloon cavity 150 or vice-versa, such as through apertures in inner balloon wall 156. This may be accomplished for a number of reasons such as to drain a cavity (e.g., inner balloon cavity 162), to mix fluid from one cavity with another, aid in heat transfer between multiple cavities, and/or to attain desired echogenic or acoustic properties of balloon member 140.

Ultrasound emitting element 170 is positioned within inner balloon 154 and is arranged to actively emit ultrasound energy through a fluid positioned with inner balloon cavity 162, inner balloon wall 156, a fluid positioned within outer balloon cavity 150, and/or outer balloon wall 144, towards a thrombosis proximate to the balloon member 140. In some instances, at least one or all of the fluids positioned within inner balloon cavity 162 and/or outer balloon cavity 150 and/or inner balloon wall 156, outer balloon wall 144, and/or surfaces thereof are arranged to aid in the transmission of ultrasound energy from ultrasound emitting element 170 towards a thrombosis proximate to balloon member 140. For example, fluids contained within inner balloon cavity 162 and/or outer balloon cavity 150 may be arranged so as to have similar acoustic impedances so as to limit the amount of ultrasound energy that is reflected rather than transmitted through portions of balloon member 140. In some instances, at least one coupling member may be incorporated into balloon member 140 so as to decrease the amount of ultrasound reflected by portions of balloon member 140.

The ultrasound emitting element 170 can comprise any ultrasound emitting device apparent to one of ordinary skill in the art to be suitable for the present disclosure. For example, ultrasound emitting element 170 may comprise a piezoelectric material that, when excited by an electric field, contracts or expands. When the electric field is reversed, the effect on the piezoelectric material is also reversed, and if the field oscillates the material cyclically contracts and expands causing a vibration. For example, the piezoelectric material may comprise a quartz or lead zirconate titanate or a synthetic ceramic, to name just a few non-limiting examples. Ultrasound emitting element 170 may also be a number of shapes. For example, ultrasound emitting element 170 may be in a rectangular, cylindrical, or hollow cylindrical shape, to name a few non-limiting examples.

In some instances, fluid contained within inner balloon cavity 162 and/or outer balloon cavity 150 may be arranged to limit the absorption of ultrasound energy. For example, fluid positioned within inner balloon cavity 162 may be arranged to absorb nominal ultrasound energy. However, in some instances the fluid contained with inner balloon cavity 162 and/or outer balloon cavity 150 may be arranged to absorb large amounts of ultrasound energy. For example, fluid positioned within outer balloon cavity 150 may be arranged to absorb ultrasound energy so as to increase the transmission of ultrasound energy to a thrombosis and/or to microbubbles, to name a few non-limiting examples. A fluid may also be arranged to absorb ultrasound energy so that the fluid can be rapidly heated upon the application of ultrasound energy.

In some instances, portions of balloon member 140 are arranged to facilitate heat transfer between portions of balloon member 140, such as inner balloon wall 156, and ultrasound emitting element 170. For example, in some embodiments, ultrasound emitting element 170 is positioned within inner balloon cavity 162 and is arranged for heat transfer between ultrasound emitting element 170 and the fluid positioned within inner balloon cavity 162. In some instances, it may be desired that ultrasound emitting element 170 be capable of transferring heat into the fluid positioned within inner balloon cavity 162. This may be desired for a number of reasons such as increasing the temperature of the fluid positioned within inner balloon cavity 162 for heating of the fluid positioned within outer balloon cavity 150 and/or for heating the thrombus and/or tissue surrounding balloon member 140.

In some instances, ultrasound emitting element 170 is arranged so as to heat thrombus, tissue, and/or fluid positioned within inner balloon cavity 162 and/or outer balloon cavity 150 to a temperature at and/or above 35° C. Additionally, or alternatively, ultrasound emitting element 170 can be arranged so as to heat thrombus, tissue, and/or fluid to a temperature at and/or below 45° C. In some embodiments, portions of balloon member 140 are arranged for cooling ultrasound emitting element 170 below a critical threshold that may cause discomfort and/or injury to the patient and/or damage to portions of treatment system 100.

It is preferred in some embodiments to heat a portion of balloon member 140 and the thrombus and/or tissue adjacent to balloon member 140 to a temperature at and/or above 35° C. By heating balloon member 140, thombus, and/or tissue, the temperature of a therapeutic agent released from outer balloon wall 144 of balloon member 140 may remain at a temperature at and/or above 35° C. for a longer period of time before being cooled by the surrounding mass of thrombus and/or tissue. Advantageously, this can improve the ability of the therapeutic agent to treat the thrombus and, in some instances, completely reduce the thrombus. It is also believed that providing ultrasound energy provides a mixing effect that increases the dispersion and binding of a therapeutic agent, such as a thrombolytic, within the thrombus and improves thrombus reduction.

In some embodiments, portions of balloon member 140 are arranged to resist heat transfer. For example, inner balloon wall 156 may comprise an insulator that resists heat transfer from a fluid positioned within inner balloon cavity 162 to a fluid positioned within outer balloon cavity 150. Additionally, or alternatively, at least one or all surfaces of a portion of balloon member 140 may be arranged for resisting heat transfer. For example, inner surface 160 of inner balloon wall 156 can be arranged to have a thermally reflective coating so as to reflect heat away from inner balloon wall 156.

FIG. 3 illustrates a cross-sectional view of catheter 102 along line 3-3 of FIG. 2. In some embodiments catheter 102 comprises an outer wall 110 having an outer surface 112 and an inner surface 114 that defines a catheter lumen 116. In some instances catheter 102 also comprises a first tubular member 118 defining a first tubular lumen 120, a second tubular member 122 defining a second tubular lumen 124, a third tubular member 126 defining a third tubular lumen 128 and/or a fourth tubular member 130 defining a fourth tubular lumen 132.

First, second, third and/or fourth tubular member 118, 122, 126 and/or 130 may be arranged in various configurations within outer wall 110 of catheter 102. For example, first, second, third and/or fourth tubular members 118, 122, 126, 130 may be coupled to one another at their outer surfaces, such as is illustrated in FIG. 3. In other embodiments, first, second, third and/or fourth lumens 120, 124, 128 and/or 132 may be defined by outer wall 110 of the catheter 102. Additionally, or alternatively, at least one and/or all of first, second, third and/or fourth tubular members 118, 122, 126, and/or 130 can be positioned within one another, such as coaxially.

In several embodiments, tubular lumens 120, 124, 128 and/or 132 fluidly communicate with at least one and/or all balloon cavities 152, 162 of balloon member 140. In some instances, first tubular lumen 120 of first tubular member 118 fluidly communicates with outer balloon cavity 150 through a first lumen opening 134 so that a fluid may flow from proximal end region 104 of catheter 102 through first tubular lumen 120 out of first lumen opening 134 and into outer balloon cavity 150 of outer balloon 142, or vice-versa. Furthermore, in some embodiments, treatment system 100 is arranged such that a fluid can flow from proximal end region 104 through first tubular lumen 120 and first lumen opening 134 into outer balloon cavity 150 and out of apertures 152.

In some instances, a second tubular lumen 124 fluidly communicates with inner balloon cavity 162 of inner balloon 154. For example, portions of treatment system 100 can be arranged such that a fluid may flow from proximal end region 104 of catheter 102 through second tubular lumen 124 out of a second lumen opening 136 into inner balloon cavity 162 so as to inflate inner balloon 154 of balloon member 140. In some embodiments a third lumen opening 138 (illustrated in FIG. 7) permits the circulation of fluid into and/or out of inner balloon cavity 162. For example, portions of treatment system 100 can be arranged such that a fluid may flow from proximal end region 104 through second tubular lumen 124, out of second lumen opening 136 into inner balloon cavity 162, and then into third lumen opening 138 and proximally through third tubular lumen 128 towards proximal end region 104 of catheter 102, or vice versa.

In some instances circulation of a fluid through inner balloon cavity 162 through one or more of tubular lumens 124 and/or 128 and the corresponding lumen openings 136 and/or 138 may be desired for temperature control. For example, fluid may be circulated to appropriately cool an ultrasound emitting element 170 positioned within inner balloon cavity 162 and/or heat a fluid positioned within outer balloon cavity 150. Fluid may be positioned within inner balloon cavity 162 and/or circulated into and/or out of inner balloon cavity 162 for heating inner balloon wall 156 which heats a fluid positioned within outer balloon cavity 150. For example, in some instances it is preferred that a therapeutic agent positioned within outer balloon cavity 150, thrombus, and/or tissue adjacent to balloon member 140 is heated to a preferred temperature between 35° C. and 45° C. prior to releasing the therapeutic agent out of outer balloon cavity 150 through apertures 152 in outer balloon wall 144.

In some instances, at least one and/or all lumens 124, 128, 132 of the tubular members 122, 126, 130 can be arranged to receive wires 172 for powering ultrasound emitting element 170. For example, third tubular lumen 128 of third tubular member 126 can be arranged to retain wires 172 from proximal end region 104 of catheter 102 to distal end region 106 for electrically coupling ultrasound emitting element 170 to a therapy control system, such as drive electronics system 200 illustrated in FIG. 9. In some embodiments, wires for powering the ultrasound emitting element 170 are embedded in one or more of the walls of the tubular members 118, 122, 126 and/or 130. Additionally or alternatively, in some instances at least one and/or all of lumens 120, 124, 128, 132 can be arranged to receive a guide wire 180 to aid in the controlled insertion and/or retrieval of catheter 102 into and/or out of the body of a patient. For example, in some instances fourth tubular member 130 may define fourth tubular lumen 132 arranged to receive guide wire 180, and may communicate with opening 182 on outer surface 112 of outer wall 110 of catheter 102 so that guide wire 180 may be inserted into catheter 102 at a location between proximal end region 104 and distal end region 106 of catheter 102. The catheter may be the standard type, with guide wire 180 extending through the length of catheter 102 and from proximal end region 104 of catheter 102, or, in some instances, the catheter 102 may be of the rapid exchange type. In some embodiments, guide wire 180 is arranged to power ultrasound emitting element 170, such as by electrically coupling guide wire 180 and a second wire to ultrasound emitting element 170 and applying a voltage difference across guide wire 180 and second wire.

Figure 9:
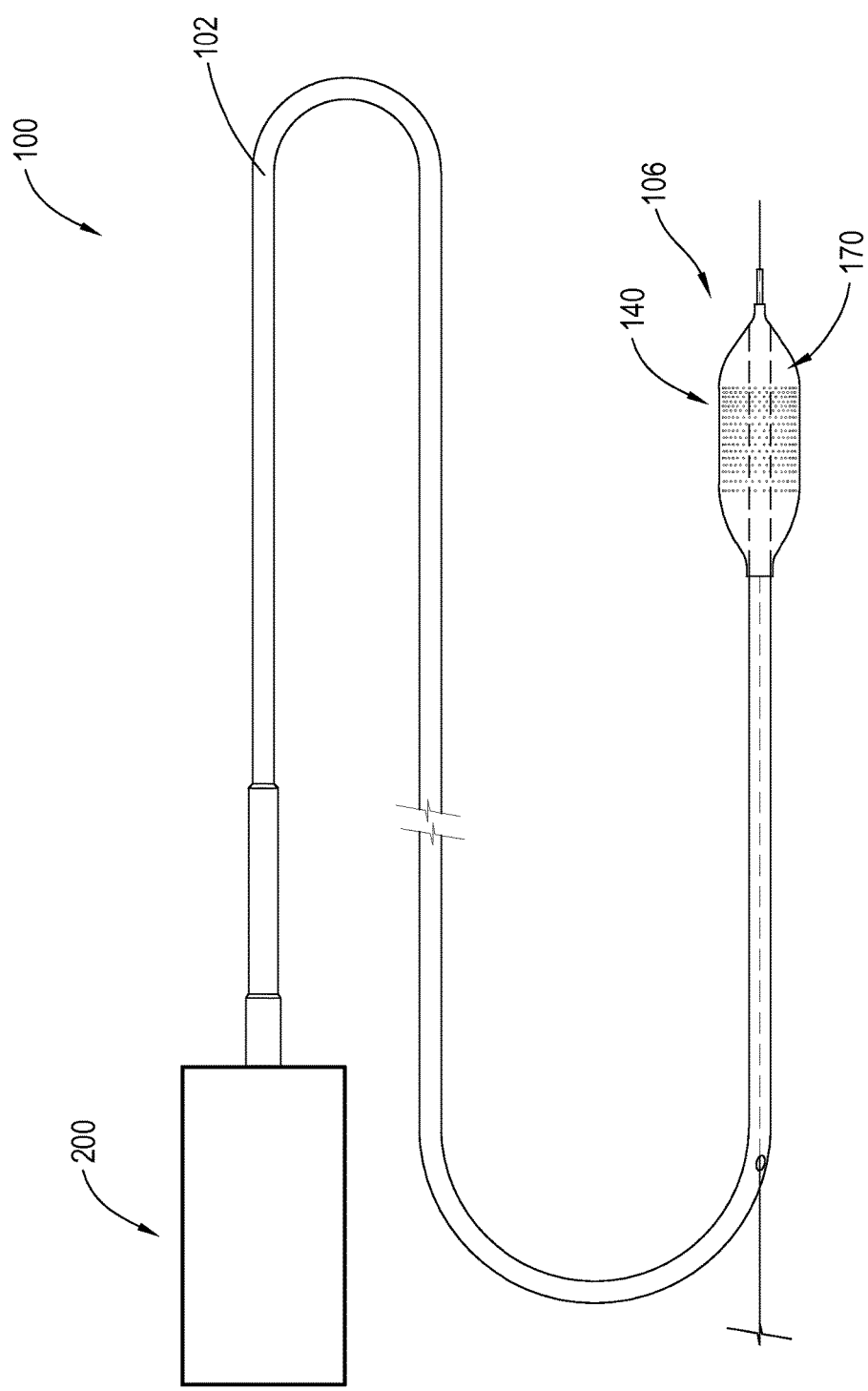
FIG. 9 is a plan view of one embodiment of a treatment system having a catheter, a balloon member, and a therapy control system.

A therapy control system, such as a drive electronics system 200 illustrated in FIG. 9, may provide electrical energy to ultrasound emitting element 170 so that ultrasound emitting element 170 actively emits ultrasound energy. In some instances, the therapy control system provides a voltage excitation so as to drive ultrasound emitting element at a frequency at and/or above 20 kHz and/or below 20 MHz. In some embodiments, the therapy control system drives ultrasound emitting element at a frequency at and/or above 100 kHz and/or below 10 MHz. More preferably, in some instances, ultrasound emitting element 170 is driven at a frequency at and/or below 4 MHz. In some arrangements, ultrasound transducer 170 is arranged to be driven at a frequency between 100 kHz and 4 MHz.

Therapy control system, such as drive electronics system 200, may also include the appropriate pumps, pressurizers, and/or indeflators for inflating outer balloon 142 and/or inner balloon 154 of balloon member 140. In some instances, therapy control system automatically inflates outer balloon 142 and inner balloon 154 and provides power to ultrasound emitting element 170. Additionally, or alternatively, therapy control system may control the temperature in at least one and/or all portions of balloon member 140. For example, therapy control system may control the temperature of fluids positioned within outer balloon cavity 150 and/or inner cavity 162, such as within a range between 35° C. and 45° C. In some instances, therapy control system controls the temperature of ultrasound emitting element 170 and/or the power being provided to ultrasound emitting element 170 for heating portions of balloon member 140, such as fluid positioned within cavities 162 and/or 150. This may be desired so as to prevent ultrasound emitting element 170 from overheating and/or damaging portions of treatment system 100 and/or causing injury or discomfort to the patient. Similarly, in some instances, therapy control system may be arranged to control the power supplied to ultrasound emitting element 170 to control the temperature of a fluid positioned within inner balloon cavity 162. In several embodiments, the temperature of portions of treatment system 100 is controlled without the use of temperature sensors. For example, the treatment control system may approximate the temperature of a fluid positioned within outer balloon cavity 150 by performing a calculation or a series of calculations using measured and/or entered data such as the properties of fluids flowing through treatment system 100, flow rates of fluids, power supplied to ultrasound emitting element 170, and/or the thermal conductivity (R-value) of portions of catheter 102 and/or balloon member 140, to name a few non-limiting examples.

In additional to the benefits mentioned above, use of a balloon, such as a multiple-wall balloon with apertures in an outer wall, to deliver a therapeutic agent is beneficial because it can stop and/or reduce flow within the vessel so as to prevent therapeutic agent washing away from the treatment site. A balloon also aids in pressurized delivery of the therapeutic agent into the clot and/or with the transmission of ultrasound energy from balloon member 140 into the blood clot. A balloon can also retain portions of the clot in proximity to the therapeutic agent and/or the ultrasound so as to continue to treat (e.g., reduce) loose portions of the blood clot. Additionally, as the clot begins to dissolve, the balloon can continue to expand and maintain contact with the vessel wall. Use of weeping balloons such those disclosed in U.S. Pat. No. 8,034,022, application Ser. No. 12/411,106 titled Weeping Balloon Catheter, by Scott E. Boatman and assigned to Cook Medical Technologies LLC, are useful for achieving precise and even delivery of therapeutic solution volume and are incorporated by reference herein.

In some instances, the therapeutic agent comprises an antithrombotic agent. An antithrombotic agent is any agent that inhibits or prevents thrombus formation within a body vessel, or chemically breaks down a blood clot or thrombus in existence. Types of antithrombotic agents include anticoagulants, antiplatelets, and fibrinolytics. Examples of antithrombotics include but are not limited to anticoagulants such as Factor Xa, Factor VIIa and tissue factor inhibitors; antiplatelets such as glycoprotein IIb/IIIa, thromboxane A2, ADP-induced glycoprotein IIb/IIIa, and phosphodiesterase inhibitors; and fibrinolytics such as plasminogen activators, thrombin activatable fibrinolysis inhibitor (TAFI) inhibitors, and other enzymes which cleave fibrin. Further examples of potentially suitable antithrombotic agents include anticoagulants such as heparin, low molecular weight heparin, covalent heparin, synthetic heparin salts, Coumadin, bivalirudin (hirulog), hirudin, argatroban, ximelagatran, dabigatran, dabigatran etexilate, D-phenalanyl-L-poly-L-arginyl, chloromethy ketone, dalteparin, enoxaparin, nadroparin, danaparoid, vapiprost, dextran, dipyridamole, omega-3 fatty acids, vitronectin receptor antagonists, DX-9065a, CM 083, JTV-803, razaxaban, BAY 59-7939, and LY-51, 7717; antiplatelets such as eftibatide, tirofiban, orbofiban, lotrafiban, abciximab, aspirin, ticlopidine, clopidogrel, cilostazol, dipyradimole, nitric oxide sources such as sodium nitroprussiate, nitroglycerin, S-nitroso and N-nitroso compounds; fibrinolytics such as alfimeprase, alteplase, anistreplase, reteplase, lanoteplase, monteplase, tenecteplase, urokinase, streptokinase, or phospholipid encapsulated microbubbles; as well as endothelial progenitor cells or endothelial cells.

In some embodiments, treatment system 100 is arranged to release microbubbles in proximity to the blood clot. It has been experimentally determined that microbubbles that receive ultrasound energy from external sources enter into cavitation, either stable cavitation with continuous application of ultrasound energy, or temporary cavitation until the microbubble bursts. Generally ultrasound devices with standard transducers that operate in the range of 2 to 12 MHz are suitable. Microbubbles that are cavitating have been found to be increasingly effective at destroying the fibrin web of a thrombus over microbubbles that are not cavitating, thus interrupting the physical structure of the thrombus and allowing access for the antithrombotic agent to act upon the thrombus. As discussed above, microbubbles are of a small enough size (nominally about one to two microns) to enter the interior of the thrombus and the fibrin web and locally dissolve the fibrin web, which assists in the degradation of the thrombus.

With continued exposure to microbubbles, preferably energized by incident ultrasound energy, the thrombus is systematically degraded or dissolved to provide increased blood flow through the localized portion of the vasculature due to the removal of the localized head loss. The combination of the compression placed onto the thrombus by the expanded walls of the balloon as well as other practices of mechanical debulking of the thrombus, and the cavitating microbubbles entering into the thrombus causes the thrombus to degrade and reestablishes suitable blood flow through the lumen and the localized application of antithrombotic bioactive agents thereto. Further, the reduction in size of the thrombus additionally reduces the likelihood that a relatively large chunk could break off and eventually flow to the heart and lungs. In some embodiments, a suitable filter or basket, such as the Gunther Tulip™ Vena Cava Filter, sold by Cook Medical, may be used in conjunction with, or attached to the treatment system 100 to prevent migration of any chunks or fragments of the thrombus from traveling away from the site in an unintended direction during or following the procedure. In some embodiments, the filter or basket may be configured to be within the same component of the device.

Figure 8:
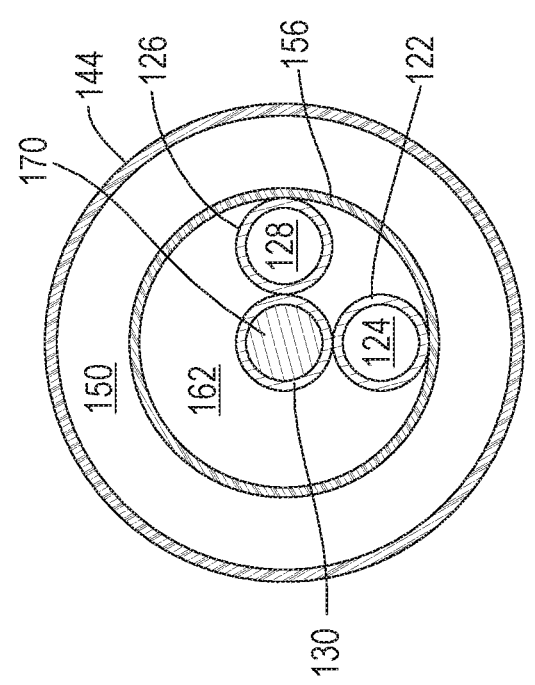
FIG. 8 is a cross-sectional view along 8-8 of the balloon member in FIGS. 7a and 7b.

FIGS. 5 and 6 illustrate another embodiment of a treatment system 100 arranged for treating a blood clot positioned within a blood vessel of a patient. As illustrated in FIG. 5, ultrasound emitting element 170 is positioned on a surface of catheter 102 such as the outer surface of fourth tubular member 130. In other embodiments, ultrasound emitting element 170 may be positioned within a lumen defined by catheter 102. For example, as illustrated in FIGS. 7 and 8, ultrasound emitting element 170 may be positioned within fourth tubular lumen 132 of fourth tubular member 130 of catheter 102.

In some instances in which ultrasound emitting element 170 is positioned within a lumen of catheter 102, ultrasound emitting element 170 can be moveably positioned within the lumen. For example, in some embodiments, ultrasound emitting element 170 may be slidably positioned within the lumen including inserted and/or removed from catheter 102 through the lumen, such as fourth tubular lumen 132. In these instances when ultrasound emitting element 170 is actively emitting ultrasound, the ultrasound travels through the tubular member defining the lumen retaining ultrasound emitting element 170, into inner balloon cavity 162, through inner balloon wall 156, into outer balloon cavity 150, and out of outer balloon wall 144 so as to interact with the therapeutic agent released from outer balloon wall 144 and/or interact with the blood clot positioned in the blood vessel of the patient. Movement of the ultrasound emitting element 170 may be desired so that ultrasound emitting element 170 may be subsequently inserted into a lumen of catheter 102 and/or a cavity of balloon member 140 after positioning of balloon member 140. Additionally, or alternatively, movement of ultrasound emitting element 170 may be desired so as to direct ultrasound energy towards particular locations of thrombus and/or tissue adjacent to balloon member 140.

It should also be appreciated, that ultrasound emitting element 170 may also be positioned within a wall of a portion of catheter 102 and/or may connect portions of catheter 102 to one another. For example, ultrasound emitting element 170 may connect a distal portion of catheter 102 to a proximal portion. Ultrasound emitting element 170 may also define a lumen for receiving a guide wire and/or a fluid, to name a few non-limiting examples.

Treatment system 100 and portions thereof may be constructed with materials and methods apparent to those of ordinary skill in the art to be suitable for the above described embodiments. For example, polymers commonly found in medical catheters may be used to form catheter 102, such as silicone, to name one non-limiting example. Additionally, the balloon may be a compliant or non-compliant balloon material, depending on the application.

Connector 190 may include one or more connectors to fluidly couple lumens of catheter 102 to pumps, pressurizers, and/or indeflators, to name a few non-limiting examples. For example, connector 190 may include one or more Luer Lock type connectors. Connector 190 may also comprise electrical connectors and/or contacts for electrically coupling a power supply to wires 172 so as to provide electrical power to ultrasound emitting element 170. For example, connector 190 may include a BNC type electrical connector.

Method of Use

Figure 10:
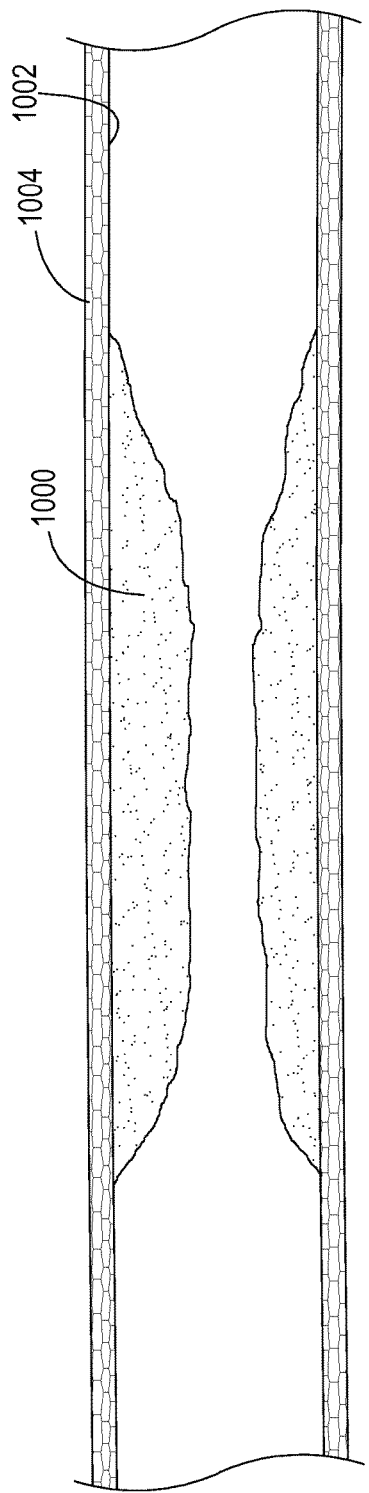
FIGS. 10, 11, 12, 13, 14 and 15 illustrate a method of using a treatment system disclosed herein.
Figure 11:
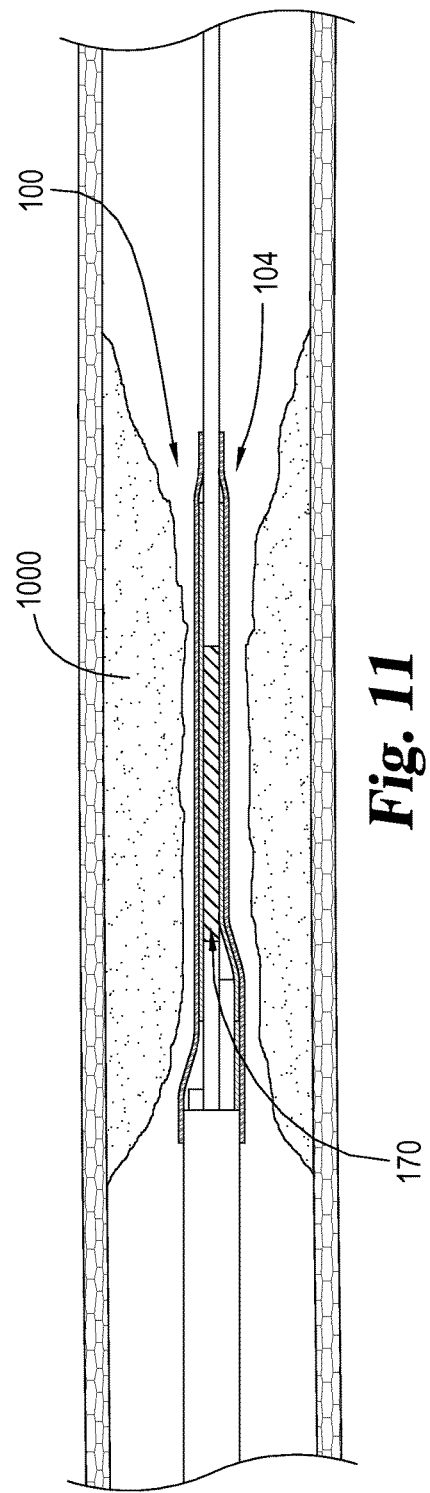

FIGS. 10, 11, 12, 13, 14, and 15 illustrate one method of use of an embodiment of a treatment system for treating a blood clot in a blood vessel of a patient. FIGS. 10-15 illustrate a partially occluded vessel; however, it should be appreciated that fully occluded vessels may also be treated with the disclosed embodiments and methods. As illustrated in FIG. 10, a blood clot 1000 is attached an inner surface 1002 of a vessel wall 1004. Treatment system 100, such as that described above, may be advanced into a position adjacent to blood clot 1000. For example, balloon member 140 and/or ultrasound emitting element 170 may be positioned adjacent to blood clot 1000 in a single and/or multiple movements of treatment system 100 and/or portions thereof.

Figure 12:
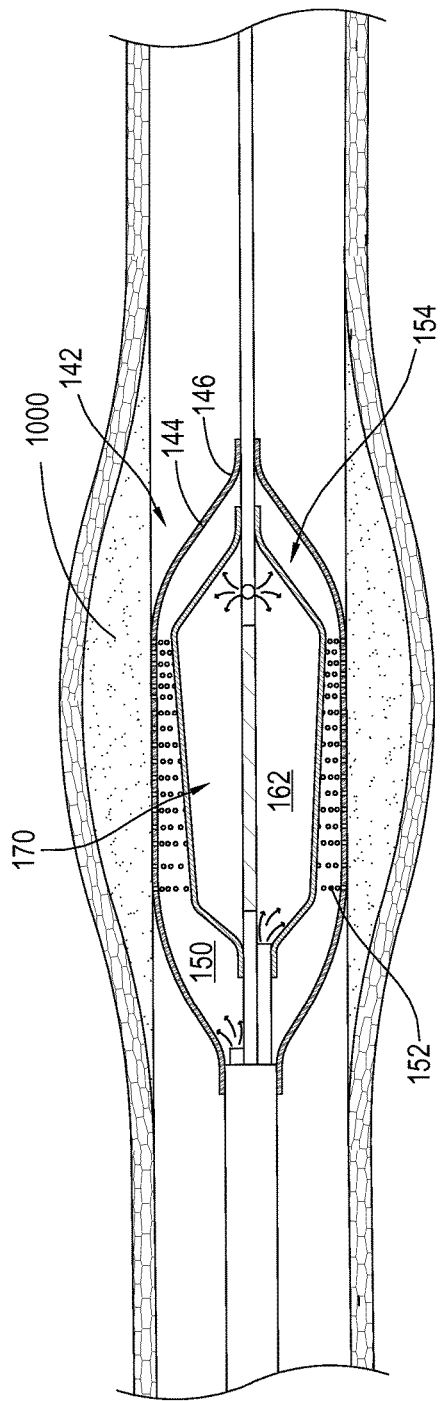

Once balloon member 140 and/or ultrasound emitting element 170 are positioned adjacent to blood clot 1000, outer balloon 142 may be inflated as illustrated in FIG. 12 to contact outer surface 146 of outer balloon wall 144 with portions of blood clot 1000 and/or compress blood clot 1000 against inner surface 1002 of vessel wall 1004. Prior to, during and/or after inflation of outer balloon 142, inner balloon 154 may be inflated so as to pressurize fluid positioned within outer balloon cavity 150 and/or push fluid out of outer balloon cavity 150 and/or apertures 152 towards blood clot 1000. In some instances, fluid within outer balloon cavity 150 is additionally, or alternatively, pressurized by a lumen in fluid communication with outer balloon cavity 150. For example, a pump, pressurizing device, and/or indeflator may be used to pressurize fluid within a lumen in fluid communication with outer balloon cavity 150.

In some instances, inner balloon cavity 162 may also be inflated so as to provide a fluid around ultrasound emitting element 170 to cool ultrasound emitting element 170. Alternatively or additionally, inner balloon cavity 162 may be inflated with a fluid arranged to change and/or control the temperature of a fluid positioned within outer balloon cavity 150 of outer balloon 142.

Figure 13:
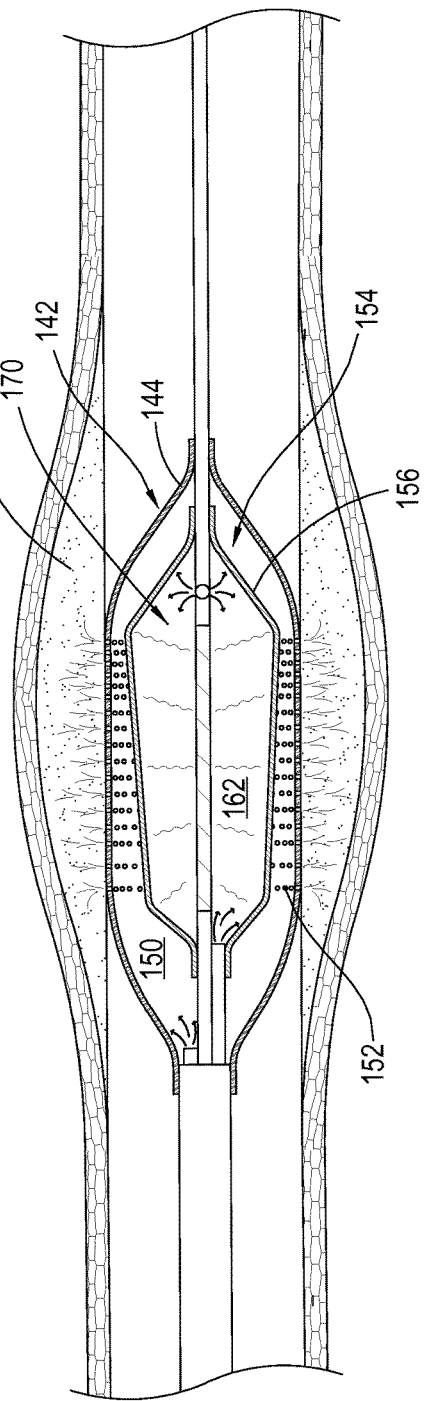

When both outer balloon 142 and inner balloon 154 are inflated, ultrasound emitting element 170 is activated (as illustrated in FIG. 13) and ultrasound is transmitted through the fluid positioned within inner balloon cavity 162, through inner balloon wall 156, into outer balloon cavity 150, and through outer balloon wall 144 into blood clot 1000, so as to increase penetration of a therapeutic agent being released from apertures 152 into blood clot 1000 and/or increase binding of a therapeutic agent with a plasminogen receptor sites within blood clot 1000.

Figure 14:
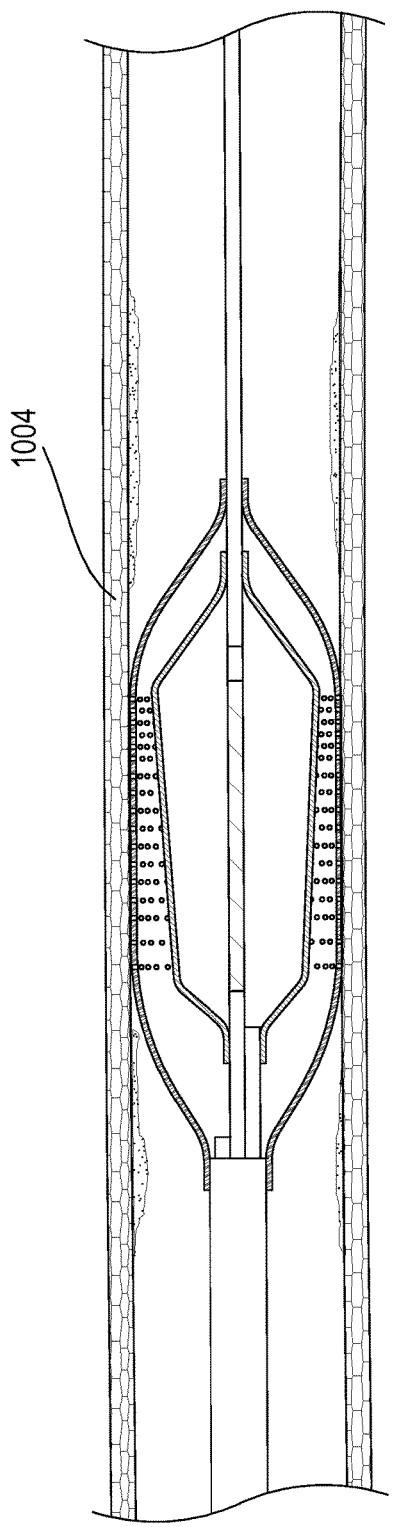
Figure 15:
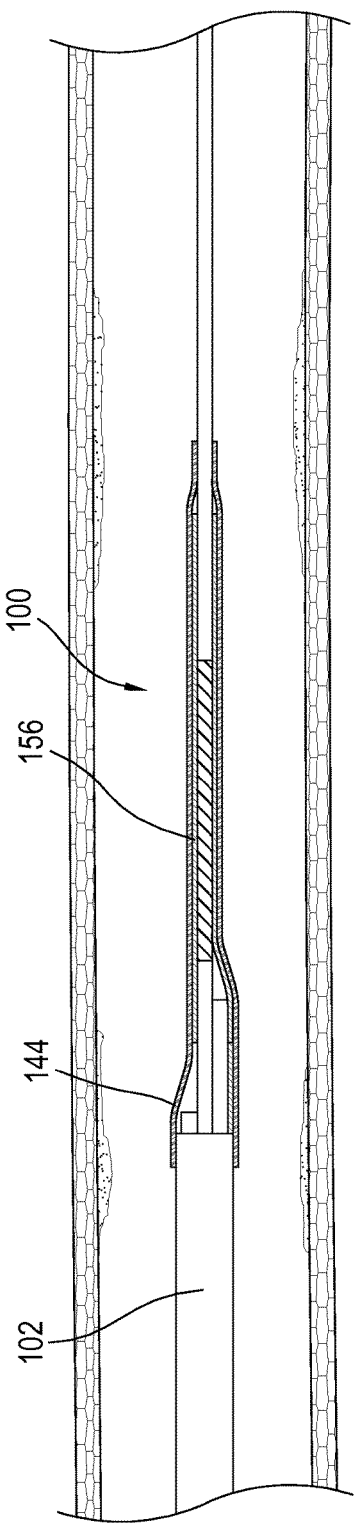

After delivery and/or release of a therapeutic agent and/or use of ultrasound to treat (e.g., reduce) blood clot 1000, vessel wall 1004 elastically returns towards a normal arrangement as illustrated in FIG. 14. When an operator is satisfied with the vessel patency, outer balloon 142 and inner balloon 154 may be deflated so as to conform outer balloon wall 144 and inner balloon wall 156 along portions of catheter 102, giving treatment system 100 a lower profile for removal from the blood vessel of the patient.

Figure 16:
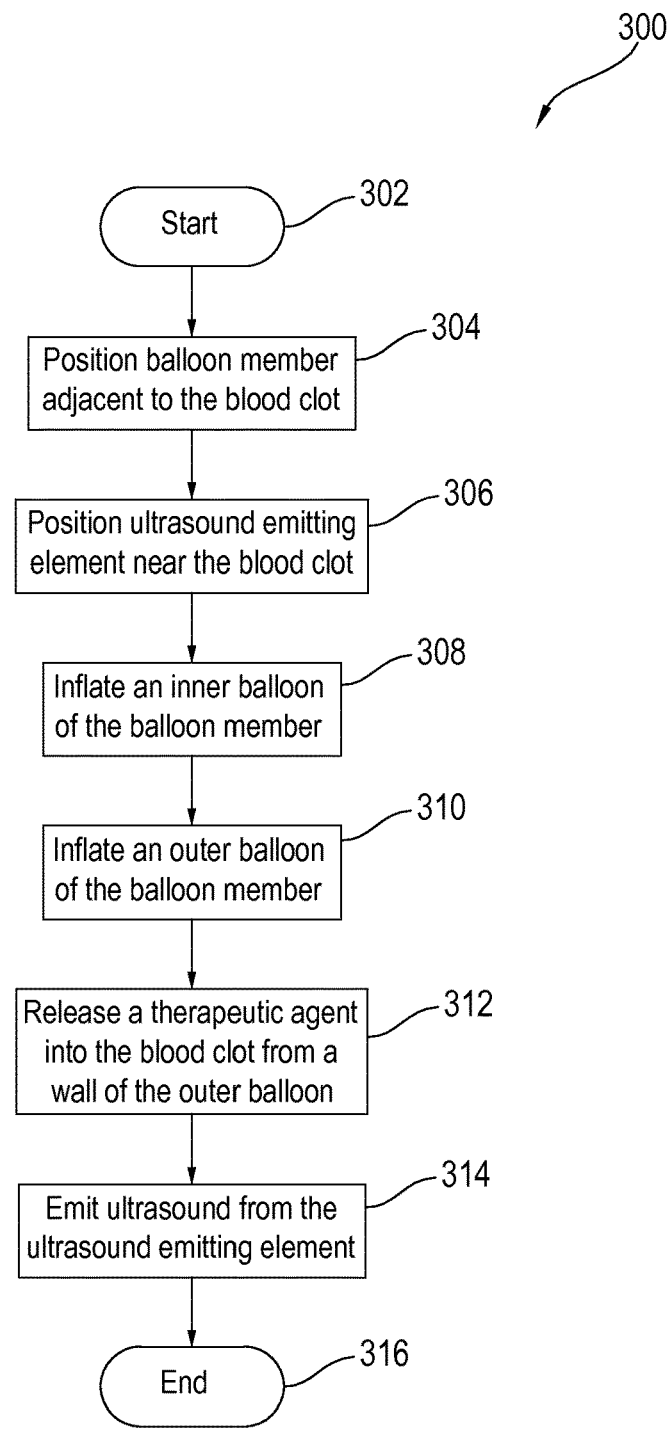
FIG. 16 illustrates a method of treating a blood clot positioned within a blood vessel of a patient.

A technique for treating a blood clot in a blood vessel will now be described with reference to flowchart 300 illustrated in FIG. 16. To aid in the explanation, this method will be described with reference to the embodiments illustrated in FIGS. 1-4, but it should be recognized that this technique can be used with other embodiments or blood clot treatment systems. In stage 302, treatment system 100 is obtained or otherwise provided in any number of manners. For instance, treatment system 100 can be purchased from a medical device manufacturer or supplier. Alternatively, a doctor may provide treatment system 100 to a patient for use within the vasculature or within other systems such as the gastrointestinal tract, genitourinary system and sinus cavities of the patient.

After stage 302, balloon member 140 is positioned adjacent to the blood clot in the vessel of the patient. In some instances, balloon member 140 can be positioned within the portion of the blood vessel being partially and/or completely occluded by the blood clot such that when balloon member 140 is inflated, outer surface 146 of outer balloon wall 144 contacts the blood clot. However, in some instances, balloon member 140 may be positioned in the vessel in a location proximal or distal of the blood clot. For example, balloon member 140 may be positioned proximal of the blood clot and have a distally firing ultrasound emitting element 170 and/or distally positioned apertures 152 for treating the blood clot positioned distally of balloon member 140. International application number PCTUS2011/022672 (WO2011/094379 A1) to McIntosh et al discloses embodiments of distally firing ultrasound and distally positioned apertures in balloons and is incorporated by reference herein. In the present example, distal end region 106 of catheter 102 upon which balloon member 140 is mounted is advanced to a location proximate to the blood clot.

In some embodiments in which ultrasound emitting element 170 is moveable independent of balloon member 140, ultrasound emitting element 170 can be positioned near the blood clot, such as in stage 306. For example, in some embodiments, ultrasound emitting element 170 is slidably positionable within a lumen of catheter 102. Therefore, distal end region 106 of catheter 102 may be positioned before, during, and/or after positioning of ultrasound emitting element 170 near the blood clot.

After balloon member 140 is in position adjacent to the blood clot and optionally after ultrasound emitting element 170 is positioned near the blood clot, inner and outer balloons 154 and 142 of balloon member 140 are inflated in stages 308 and 310. Stages 308 and 310 may occur in any order. For example, the inflation of inner balloon 154 may occur before, during, and/or after inflation of outer balloons 154. In some instances, the inner balloon is inflated first to press outer balloon wall 144 against the blood clot so that when the therapeutic agent is delivered from apertures 152 it enters the blood clot.

In some embodiments, outer balloon 142 is inflated first, being filled with a therapeutic agent, and then inner balloon 154 is inflated second so as to push the therapeutic agent positioned within outer balloon cavity 150 through apertures 152 in outer balloon wall 144 and into the blood clot. In some instances in which inner balloon 154 is inflated after outer balloon 142, inner balloon 154 is rapidly inflated so as to achieve a greater pressure within outer balloon cavity 150 and forcibly eject fluid from apertures 152. In some embodiments, rapid inflation of inner balloon 154 increases the velocity at which therapeutic agent exits apertures 152 and subsequently enters the adjacent thrombus and/or tissue. This can improve the penetration of the therapeutic agent into the thrombus and, in some instances, help to more quickly and/or further clear the thrombus from the vessel.

After stages 302 and 304, and after at least one and/or all of stages 308 and 310, therapeutic agent is released from outer balloon wall 144 into the blood clot. As discussed above, the therapeutic agent may initially be positioned on outer surface 146 of outer balloon wall 144, in outer balloon wall 144, within outer balloon cavity 150, and/or external of the patient prior to inflation stages 308 and/or 310. Preferably, the therapeutic agent is released after contact of outer balloon wall 144 with the blood clot.

After stage 306, ultrasound is emitted from ultrasound emitting element 170, in stage 314. Stage 314 may occur before, during, and or after stages 308, 310, and/or 312. In some instances, stage 314 is synchronized with at least one and/or all other stages of the method for treating a blood clot in the body of a patient. For example, stage 314 may be initiated after stage 308 and/or 310 so that outer balloon wall 144 is in abutting contact with the blood clot, so as to aid in the transmission of ultrasound energy from treatment system 100 into the blood clot. Once the blood clot is sufficiently removed and/or reduced, the process concludes in stage 316.

While at least one embodiment has been illustrated and described in detail in the drawings and foregoing description, the same is to be considered as illustrative and not restrictive in character, it being understood that the preferred embodiment has been shown and described and that all changes, equivalents, and modifications that come within the spirit of the inventions defined by following claims are desired to be protected. For example, other embodiments can have more or fewer balloon members, balloon walls, lumens, cavities, and/or ultrasound emitting elements than the embodiments illustrated above. It will be evident from the specification that aspects or features discussed in one context or embodiment will be applicable in other contexts or embodiments. All publications, patents, and patent applications cited in this specification are herein incorporated by reference as if each individual publication, patent, or patent application were specifically and individually indicated to be incorporated by reference and set forth in its entirety herein.

The invention claimed is:

1. A medical device for treating a blood clot in a blood vessel, comprising:
    a multi-lumen catheter having a first lumen, a second lumen, and a third lumen each extending from a proximal end region of the multi-lumen catheter to a distal end region of the multi-lumen catheter;
    a balloon member positioned on the multi-lumen catheter, the balloon member having an inner balloon with an inner balloon wall and an outer balloon with an outer balloon wall;
    an ultrasound emitting element positioned within the balloon member; and
    a therapy control system arranged to provide electrical energy to the ultrasound emitting element;
    wherein the first lumen is in fluid communication with an outer-balloon cavity defined between the outer balloon wall and the inner balloon wall;
    wherein the second and third lumens are in fluid communication with an inner-balloon cavity within the inner balloon and with the therapy control system;
    wherein the ultrasound emitting element is arranged for actively emitting ultrasound;
    wherein the therapy control system controls the temperature of fluid positioned within the outer balloon cavity by circulating fluid through the second and third lumens and adjusting power supplied to the ultrasound emitting element; and
    wherein the therapy control system adjusts power supplied to the ultrasound emitting element to control temperature of fluid positioned within the outer balloon cavity to between 35° C. and 45° C.

2. The medical device of claim 1, wherein:
    the ultrasound emitting element is positioned on an outer surface of the catheter.

3. The medical device of claim 1, wherein:
    the ultrasound emitting element is positioned in a wall of the catheter.

4. The medical device of claim 1, wherein:
the ultrasound emitting element is positioned within a lumen of the catheter and movable within the catheter.

5. The medical device of claim 1, wherein:
the ultrasound emitting element is arranged to heat tissue or thrombus adjacent to the balloon member.

6. The medical device of claim 1, wherein:
the ultrasound emitting element is arranged to heat a fluid positioned within the balloon member.

7. The medical device of claim 6, wherein:
the balloon member is configured to transfer heat to tissue or thrombus adjacent to the balloon member.

8. The medical device of claim 1, wherein:
the outer balloon wall of the balloon member has apertures therein arranged to release a therapeutic agent.

9. The medical device of claim 8, wherein:
the apertures extend through the outer balloon wall of the balloon member and communicate with an outer balloon cavity.

10. The medical device of claim 1, wherein:
the inner balloon wall of the balloon member is arranged to transmit heat from a first fluid within an inner balloon cavity defined by said inner balloon wall to a second fluid within an outer balloon cavity defined by the outer balloon wall.

11. A medical device for treating a blood clot in a blood vessel, comprising:
a multi-lumen catheter having a first lumen, a second lumen, and a third lumen each extending from a proximal end region of the multi-lumen catheter to a distal end region of the multi-lumen catheter;
a balloon with a porous balloon wall positioned on the multi-lumen catheter and surrounding an ultrasound emitting element; and
a therapy control system arranged to circulate fluid through said second and third lumens and provide electrical energy to the ultrasound emitting element;
wherein the second and third lumens are in fluid communication within the balloon;
wherein the ultrasound emitting element is arranged for actively emitting ultrasound;
wherein the therapy control system controls the temperature of fluid positioned within the balloon by circulating fluid through the second and third lumens and adjusting power supplied to the ultrasound emitting element; and
wherein the therapy control system adjusts power supplied to the ultrasound emitting element to control temperature of fluid positioned within the balloon to between 35° C. and 45° C.

12. The medical device of claim 11, wherein:
the ultrasound emitting element is positioned on an outer surface of the catheter.

13. The medical device of claim 11, wherein:
the ultrasound emitting element is positioned in a wall of the catheter.

14. The medical device of claim 11, wherein:
the ultrasound emitting element is slidably positionable within a lumen of the catheter.

15. The medical device of claim 11, wherein:
the ultrasound emitting element is arranged to heat tissue or thrombus adjacent to the balloon.

16. The medical device of claim 11, wherein:
the ultrasound emitting element is arranged to heat a fluid positioned within the balloon.

17. The medical device of claim 16, wherein:
the balloon is configured to transfer heat to tissue or thrombus adjacent to the balloon.

18. A medical device for treating a blood clot in a blood vessel, comprising:
a catheter having a first lumen, a second lumen, and a third lumen;
a balloon member positioned on a distal portion of said catheter and having inner and outer balloons defining inner and outer balloon cavities;
an ultrasound emitting element positioned within said inner balloon cavity; and
a therapy control system arranged to provide electrical energy to the ultrasound emitting element and circulate fluid through said second and third lumens;
wherein said first, second, and third lumens each extend from a proximal end region of said catheter to a distal end region of said catheter and, said second and third lumens communicating with said inner balloon cavity and said first lumen communicating with said outer balloon cavity;
wherein said second lumen and said third lumen cooperate to circulate a temperature-control fluid between the proximal end region of said catheter and said inner balloon cavity;
wherein said ultrasound emitting element actively emits ultrasound through said inner balloon cavity, into said outer balloon cavity, and out of said outer balloon cavity into the blood clot adjacent to said outer balloon;
wherein the therapy control system controls the temperature of fluid positioned within the outer balloon cavity by circulating fluid through the second and third lumens and adjusting power supplied to the ultrasound emitting element; and
wherein the therapy control system adjusts power supplied to the ultrasound emitting element to control temperature of fluid positioned within the outer balloon cavity to between 35° C. and 45° C.

19. The medical device of claim 18, wherein:
said ultrasound emitting element is positioned on an outer surface of said catheter.

20. The medical device of claim 18, wherein:
said ultrasound emitting element is positioned in a wall of said catheter.

21. The medical device of claim 18, wherein:
said ultrasound emitting element is slidably positionable within a lumen of said catheter.

22. The medical device of claim 18, wherein:
said ultrasound emitting element is arranged to heat tissue or thrombus adjacent to said balloon member.

23. The medical device of claim 18, wherein:
said ultrasound emitting element is arranged to heat a fluid positioned within said balloon member.

24. The medical device of claim 23, wherein:
said balloon member is configured to transfer heat to tissue or thrombus adjacent to said balloon member.

25. The medical device of claim 18, wherein:
an outer balloon wall of said outer balloon has apertures therein arranged to release a therapeutic agent.

26. The medical device of claim 25, wherein:
said apertures extend through said outer balloon wall and communicate with said outer balloon cavity.

27. The medical device of claim 26, wherein:
said apertures are configured to release a therapeutic agent contained within said outer balloon cavity.

28. The medical device of claim 18, wherein:

an inner balloon wall of said inner balloon is arranged to transmit heat from a fluid within said inner balloon cavity to a fluid within said outer balloon cavity.

29. The medical device of claim 18, further comprising:
a fourth lumen within said catheter and arranged to receive at least one ultrasound wire extending to said ultrasound emitting element.

30. The medical device of claim 18, wherein:
a fourth lumen within said catheter is arranged to receive a wire guide.

31. A method of treating a blood clot in a blood vessel, comprising:
positioning adjacent to the blood clot a distal portion of a catheter having a balloon member having inner and outer balloons and an ultrasound emitting element positioned within the inner balloon;
inflating the inner balloon of the balloon member;
inflating the outer balloon of the balloon member;
heating a therapeutic agent to a temperature between 35° C. and 45° C. with the ultrasound emitting element;
releasing the therapeutic agent into the blood clot from a wall of the outer balloon;
emitting ultrasound from the ultrasound emitting element so as to increase penetration of the therapeutic agent into the blood clot and treat the blood clot; and
flowing fluid from a proximal end region of the catheter into a balloon cavity of the inner balloon through a first lumen and flowing fluid from the balloon cavity to the proximal end region through a second lumen;
wherein the therapy control system controls the temperature of fluid positioned within the outer balloon cavity by circulating fluid through the second and third lumens and adjusting power supplied to the ultrasound emitting element.

32. The method of claim 31, wherein:
said releasing a therapeutic agent is synchronized with said emitting ultrasound from the ultrasound emitting element.

33. The method of claim 32, wherein:
said releasing a therapeutic agent and said emitting ultrasound occur simultaneously.

34. The method of claim 31, wherein:
the therapeutic agent is a thrombolytic agent.

35. The method of claim 31, wherein inflating the outer balloon of the balloon member comprises flowing the therapeutic agent from the catheter into an outer balloon cavity.

* * * * *